United States Patent [19]

Deckner et al.

[11] Patent Number: 5,776,485
[45] Date of Patent: Jul. 7, 1998

[54] ENHANCED SKIN PENETRATION SYSTEM FOR IMPROVED TOPICAL DELIVERY OF DRUGS

[75] Inventors: George Endel Deckner, Trumbull; Brian Scott Lombardo, Ansonia, both of Conn.

[73] Assignee: Richardson-Vicks Inc., Shelton, Conn.

[21] Appl. No.: 469,701

[22] Filed: Jun. 6, 1995

Related U.S. Application Data

[63] Continuation of Ser. No. 390,902, Feb. 16, 1995, abandoned, which is a continuation of Ser. No. 228,167, Apr. 15, 1994, abandoned, which is a continuation of Ser. No. 111,032, Aug. 24, 1993, abandoned, which is a continuation of Ser. No. 957,752, Oct. 2, 1992, abandoned, which is a continuation of Ser. No. 778,424, Oct. 16, 1991, abandoned.

[51] Int. Cl.$^6$ .......................... A61K 9/07; A61K 31/78; A61K 47/44
[52] U.S. Cl. .................. 424/449; 514/772.3; 514/772.6; 514/789; 514/938; 514/944; 514/946
[58] Field of Search .............. 424/449; 514/772.3, 514/772.6, 789, 938, 944, 946

[56] References Cited

U.S. PATENT DOCUMENTS

| | | | |
|---|---|---|---|
| Re. 28,474 | 7/1975 | Anderson et al. | |
| 3,624,019 | 11/1971 | Anderson et al. | |
| 3,920,808 | 11/1975 | Fusaro | 424/59 |
| 3,920,810 | 11/1975 | Rankin | 424/80 |
| 4,039,501 | 8/1977 | Babcock et al. | 260/30.4 R |
| 4,307,717 | 12/1981 | Hymes et al. | 128/56 |
| 4,318,907 | 3/1982 | Kligman et al. | 424/230 |
| 4,355,028 | 10/1982 | Kligman et al. | 424/230 |
| 4,478,853 | 10/1984 | Chaussee | 424/358 |
| 4,540,568 | 9/1985 | Trager et al. | 424/81 |
| 4,599,379 | 7/1986 | Flescher et al. | 524/801 |
| 4,628,078 | 12/1986 | Glover et al. | 526/303 |
| 4,650,827 | 3/1987 | Becker et al. | |
| 4,673,704 | 6/1987 | Flesher et al. | 524/519 |
| 4,675,009 | 6/1987 | Hymes et al. | 424/449 |
| 4,704,436 | 11/1987 | Barabas | 525/326.9 |
| 4,731,242 | 3/1988 | Palinczar | 424/59 |
| 4,806,345 | 2/1989 | Bhattacharyya | 424/70 |
| 4,835,206 | 5/1989 | Farrar et al. | 524/457 |
| 4,837,019 | 6/1989 | Georgalas et al. | 424/101 |
| 4,849,484 | 7/1989 | Heard | 525/221 |
| 4,885,161 | 12/1989 | Cornell | 424/78 |
| 4,915,940 | 4/1990 | Saitoh et al. | 424/81 |
| 4,927,408 | 5/1990 | Haak et al. | 604/20 |
| 4,929,577 | 5/1990 | Cornell | 514/58 |
| 4,938,951 | 7/1990 | Leung et al. | 424/59 |
| 4,948,586 | 8/1990 | Bohm et al. | 424/406 |
| 4,954,487 | 9/1990 | Cooper et al. | 514/159 |
| 5,009,969 | 4/1991 | Miller | 424/59 |
| 5,017,367 | 5/1991 | Stojkoski | 424/63 |
| 5,043,359 | 8/1991 | Ward et al. | 514/772 |
| 5,057,560 | 10/1991 | Mueller | 524/22 |
| 5,100,658 | 3/1992 | Bolich et al | 424/70 |
| 5,100,660 | 3/1992 | Hawe et al. | 424/78.35 |
| 5,110,853 | 5/1992 | Van-Det et al. | |
| 5,147,923 | 9/1992 | Mueller | 524/555 |
| 5,169,624 | 12/1992 | Cheyney et al. | |
| 5,200,448 | 4/1993 | Robinson et al. | |
| 5,221,530 | 6/1993 | Janchitraponveg et al. | 424/70 |
| 5,232,688 | 8/1993 | Ziegler et al. | 424/59 |
| 5,302,378 | 4/1994 | Crotty et al. | |
| 5,422,118 | 6/1995 | Brown et al. | |
| 5,458,872 | 10/1995 | Durand | 424/59 |
| 5,614,178 | 3/1997 | Bloom et al. | |
| 5,618,522 | 4/1997 | Kaleta et al. | |

FOREIGN PATENT DOCUMENTS

| | | |
|---|---|---|
| 1300513 | 5/1992 | Canada. |
| 067658 | 6/1982 | European Pat. Off. |
| 228868 | 12/1986 | European Pat. Off. |
| 312208 | 9/1988 | European Pat. Off. |
| 424282 | 4/1991 | European Pat. Off. |
| 2651126 | 3/1991 | France. |
| 2071745 | 6/1982 | Japan. |
| 57091913 | 3/1990 | Japan. |
| 2236760 | 10/1990 | United Kingdom. |
| 9217159 | 10/1992 | WIPO. |
| 93/07856 | 4/1993 | WIPO. |
| 93/07903 | 4/1993 | WIPO. |

OTHER PUBLICATIONS

Sales Literature, Salcare SC92 for Cosmetic/Personal Care Applications, undated.
Sales Literature, Salcare SC91: The Cosmetic Formulator's Choice for Anionic Skin Care Products, undated.
Sales Literature, Sepigel 305, Thickening Agent for Aqueous Gels and Emulsions, undated.
Mueller Derwent of U.S. 5147923 (Sep. 15, 1992).
Mueller Derwent of U.S. 5057560 (Oct. 15, 1991).
Durand Derwent of WO/Pct 91 12222 (Aug. 22, 1991) and U.S. 5458872 (Oct. 17, 1995).
Bolich et al Derwent of US 5100658 (Mar. 31, 1992) and (EP 412705 (Feb. 13, 1991).
Leung et al Derwent of U.S. 4938951 (Jul. 3, 1990).
Bohm et al Derwent of US 4948586 (Aug. 14, 1990).
U.S.application No. 08/059.001, Deckner et al., filed May 6, 1993, which is a continuation of U.S. application No. 07/948,391, Deckner et al., filed Sep. 25, 1992, which is a continuation-in-part of U.S. application No. 07/778,423, Deckner et al., filed Oct. 16, 1991.
U.S. application No. 07/931,553, Deckner et al., filed Aug. 18, 1992, withic is a continuation of U.S. application No. 07/778,423, Deckner et al., filed Oct. 16, 1991.

(List continued on next page.)

Primary Examiner—Shep K. Rose
Attorney, Agent, or Firm—Loretta J. Henderson; David K. Dabbiere

[57] ABSTRACT

The invention involves pharmaceutical compositions for topical application comprising:

(a) a safe and effective amount of a pharmaceutical active; and (b) from about 0.05% to about 5% of a non-ionic polyacrylamide having a molecular weight of from about 1,000,000 to about 30,000,000.

15 Claims, No Drawings

OTHER PUBLICATIONS

U.S. application No. 08/079,977, Bloom et al., filed Jun. 25, 1993, which is a continuation–in–part of U.S. application No. 08/033,211, Bloom et al., filed Mar. 18, 1993, which is a continuation–in–part of U.S. application No. 07/950,527, Bloom et al., filed Sep. 25, 1992, which is a continuation in part of U.S. application No. 07/920,937, Bloom et al., filed Jul. 28, 1992.

Seppic Sepigel ®305 Thickening Aqueous Emulsions Poly Acrylamide, Iso Paraffin Agent for Gels and Sun Gel Lavreth–7 (Mar. 1991).

Cotte et al C.A. 115:239330 of EP424282 Apr. 24, 1991.

Cotter et al C.A. 115:990004 of FR 2651 126 (Mar. 1991).

Quack et al C.A. 91:216665 of GEROFFDE 2806098 (Feb. 1978).

Fusaro C.A. 84:49847 of U.S. 3920808 (Nov. 1975).

Futtterer C.A. 79: 139608 of Cosmet. Perfum 88(8): 31–33 (1973).

Isacoff C.A. 78:115119 of Cosmet. Perfum 88(2): 35–37(1973).

Woodin Derwent WO/PCT 92 1715.9 (Oct. 15, 1992) of U.S. 91/679892 (Apr. 3, 1991).

Futterer Cosmet. Perfum. 88(8): 31–33 "Theory and Practice of Artificial Tanning", 1973.

Isacoff Cosmet. Perfum. 88(2):35–37 "Polyaerylamides in Cosmetics", 1973.

Seppic Sepigel®305 "Thickening Agent for Aqueous Gels and Emulsions", Mar. 1991.

ENHANCED SKIN PENETRATION SYSTEM FOR IMPROVED TOPICAL DELIVERY OF DRUGS

This is a continuation of application Ser. No. 08/390,902, filed on Feb. 16, 1995 which is a continuation of application Ser. No. 08/228,167, filed on Apr. 15, 1994, which is a continuation of application Ser. No. 08/111,032, filed on Aug. 24, 1993, which is a continuation of application Ser. No. 07/957,752, filed on Oct. 2, 1992, which is a continuation of application Ser. No. 07/778,424, filed on Oct. 16, 1991 all now abandoned.

TECHNICAL FIELD

The present invention relates to compositions for the topical administration of drugs, especially such compositions having enhanced penetration of the drug through the skin.

BACKGROUND OF THE INVENTION

Because of the accessibility and large area of the skin, it has long been considered a promising route for the administration of drugs, whether dermal, regional, or systemic effects are desired.

The advantages of the topical route of drug administration include: avoidance of the risks and inconvenience of parenteral treatment; avoidance of the variable absorption and metabolism associated with oral treatment; continuity of drug administration, permitting use of pharmacologically active agents with short biological half-lives; potential reduction of gastrointestinal irritation in systemic administration; and treatment of curtaneous manifestations of diseases usually treated systemically.

However, the impermeability of skin is well-known, serving as a barrier to ingress of pathogens and toxic chemicals, and egress of physiologic fluids. This impermeability is the result of normal physiologic changes in developing skin. A typical cell in the epidermis is formed in the basal layer. It typically takes approximately thirty days for a cell to migrate from the basal layer of the epidermis to sloughing off and discarding at the outer layers of the stratum corneum. As the cell migrates outward from the basal layer, it progressively keratinizes until it is relatively impermeable. The result is the stratum corneum, an extremely thin surface layer (10 microns) with substantial barrier properties. The cell envelopes of the cells in the stratum corneum tend to be mainly polar lipids, such as ceramides, sterols, and fatty acids while the cytoplasm of stratum corneum cells remains polar and aqueous. Despite the close packing of the cells, some 15% of the stratum corneum is intercellular and, generally, lipid based. It is generally recognized that over the very short term, penetration occurs through the hair follicles and the sebaceous apparatus; long-term penetration occurs across cells (non-polar route). Poor penetration of many drugs across the epidermal lipid barrier has, until now, frustrated attempts to deliver clinically significant doses of many drugs by the topical route.

One route of internal delivery of drugs is by transdermal administration. Transdermal administration of drugs can be used in many instances to achieve therapeutic levels of the drugs in the systemic circulatory system, as well as for more localized internal dosing of drugs. Where such therapeutic levels of drugs can be achieved by transdermal administration, several potential advantages exist over other routes of administration. Sustained systemic delivery of drug controlled at therapeutic but below toxic levels over long periods of time with a single continuous application is often an advantage of transdermal drug administration. Potential contamination of internal tissues with undesired foreign substances or microbes, often associated with parenteral administration of drugs, is avoided with transdermal drug administration. Oral administration of many drugs is undesirable or unfeasible because the drug decomposes in the harsh environment of the gastrointestinal tract, lacks sufficient absorption from the gastrointestinal tract, or causes gastrointestinal upset or tissue damage in the gastrointestinal tract. First-pass metabolism of orally administered drugs can increase the dosage required to achieve therapeutic levels and thereby increase undesirable side effects either from the primary drug or the metabolites. Maintenance of uniform, optimal systemic levels of drugs for long periods of time is often difficult through oral administration. Such problems can often be reduced or avoided by transdermal drug administration.

Despite the substantial potential advantages for transdermal administration of drugs, relatively few drugs are so administered. The skin is a formidable barrier to the passage of most drugs. It is often necessary to provide a composition containing a skin penetration enhancing vehicle in order to provide sufficient transdermal penetration of the drug to achieve therapeutic levels of the drug at the target internal tissue. A number of skin penetration enhancing vehicles for drugs have been disclosed, including those in the following references: U.S. Pat. No. 3,536,816 issued to Kellner on Oct. 27, 1970; U.S. Pat. No. 4,006,218 issued to Sipos on Feb. 1, 1977; U.S. Pat. No. 4,124,720 issued to Wenmaekers on Nov. 7, 1978; U.S. Pat. No. 4,126,681 issued to Reller on Nov. 21, 1978; U.S. Pat. No. 4,299,826 issued to Luedders on Nov. 10, 1981; U.S. Pat. No. 4,305,936 issued to Klein on Dec. 15, 1981; U.S. Pat. No. 4,309,414 issued to Inagi, Muramatsu & Nagai on Jan. 5, 1982; U.S. Pat. No. 4,338,306 issued to Kitao & Nishimura on Jul. 6, 1982; U.S. Pat. No. 4,442,090 issued to Kakeya, Kitao & Nishimura on Apr. 10, 1984; U.S. Pat. No. 4,485,033 issued to Kitao & Nishimura on Nov. 27, 1984; U.S. Pat. No. 4,537,776 issued to Cooper on Aug. 27, 1985; U.S. Pat. No. 4,552,872 issued to Cooper, Loomans & Fawzi on Nov. 12, 1985; U.S. Pat. No. 4,557,934 issued to Cooper on Dec. 10, 1985; U.S. Pat. No. 4,573,995 issued to Chen, Chun & Enscore on Mar. 4, 1986; U.S. Pat. No. 4,626,539 issued to Aungst & DiLuocio on Dec. 2, 1986; U.S. Pat. No. 4,637,930 issued to Konno, Kawata, Aruga, Sonobe & Mitomi issued Jan. 20, 1987; U.S. Pat. No. 4,695,465 issued to Kigasawa, Ohtani, Tanaka & Hayashida on Sep. 22, 1987; European Patent Application No. 0,043,738 of The Procter & Gamble Company in the names of Wickett, Cooper & Loomans, published on Jun. 13 1982; European Patent Application No. 0,095,813 of The Procter & Gamble Company in the name of Cooper, published Dec. 7, 1983; PCT International Patent Application No. WO 87/03490 of Key Pharmaceuticals, Inc. in the names of Bodor and Loftson, published on Jun. 18, 1987; Washitake, M., T. Anmo, I. Tanaka, T. Arita & M. Nakano, "Percutaneous Absorption of Drugs from Oily Vehicles", *Journal of Pharmaceutical Sciences*, Vol. 64, No. 3 (March, 1975), pp. 397–401; Shahi, V., & J. L. Zatz, "Effect of Formulation Factors on Penetration of Hydrocortisone through Mouse Skin", *Journal of Pharmaceutical Sciences*, Vol. 67, No. 6 (June, 1978), pp. 789–792; Cooper, E. R., "Increased Skin Permeability for Lipophilic Molecules", *Journal of Pharmaceutical Sciences*, Vol. 73, No. 8 (August, 1984), pp. 1153–1156; Aungst, B. J., N. J. Rogers & E. Shefter, "Enhancement of Naloxone Penetration through Human Skin In Vitro Using Fatty Acids, Fatty Alcohols, Surfactants, Sulfoxides and Amides", *International Journal of Pharmaceutics*, Vol. 33 (1986), pp. 225–234; Green, P. G., & J. Hadgraft, "Facilitated Transfer of Cationic Drugs Across a Lipoidal Membrane by Oleic Acid and Lauric Acid", *International Journal of Pharmaceutics*, Vol. 37 (July, 1987), pp. 251–255.

It is an object of the present invention to provide novel compositions for enhancing the skin penetration of drugs.

It is a further object of the present invention to provide such compositions which provide sufficient skin penetration enhancement to achieve therapeutic levels of the drugs in target internal tissues.

It is a further object of the present invention to provide such compositions with low dermal irritation, especially in compositions requiring a low pH.

It is a still further object of the present invention to provide such compositions having good stability and good cosmetics.

SUMMARY OF THE INVENTION

The present invention relates to pharmaceutical compositions for topical application having enhanced penetration through the skin comprising:

(a) a safe and effective amount of a pharmaceutical active; and (b) from about 0.05% to about 20% of a non-ionic polyacrylamide having a molecular weight of from about 1,000,000 to about 30,000,000.

All concentrations and ratios herein are by weight of total composition and all measurements are at 25°C, unless otherwise specified.

DETAILED DESCRIPTION OF THE INVENTION

The present invention involves compositions comprising certain specific non-ionic polymers which may be applied topically to the skin and which result in improved transdermal penetration of the drugs through the skin. These compositions also have a high solvent tolerance, i.e., high level of solvents such as alcohol and other water-soluble components which may be necessary to solubilize the active can be included in the compositions.

Drug Active

The compositions of the present invention comprise a safe and effective amount of a drug active. The phrase "safe and effective amount", as used herein, means an amount of a drug high enough to significantly positively modify the condition to be treated, but low enough to avoid serious side effects (at a reasonable benefit/risk ratio), within the scope of sound medical judgement. A safe and effective amount of the drug will vary with the specific drug, the ability of the composition to penetrate the drug through the skin, the amount of composition to be applied, the particular condition being treated, the age and physical condition of the patient being treated, the severity of the condition, the duration of the treatment, the nature of concurrent therapy, and like factors.

The drug compounds present in the compositions of the present invention preferably comprise from about 0.1% to about 20% by weight of the compositions, more preferably from about 0.1% to about 10%, and most preferably from about 0.1% to about 5%. Mixtures of drug actives may also be used.

Useful drug actives in the compositions of the present invention include anti-acne drugs. Anti-acne drugs preferred for use in the present invention include the keratolytics such as salicylcic acid, sulfur, lactic acid, glycolic, pyruvic acid, urea, resorcinol, and N-acetylcysteine; retinoids such as retinoic acid and its derivatives (e.g., cis and trans); antibiotics and antimicrobials such as benzoyl peroxide, octopirox, erythromycin, tetracyclin, triclosan, azelaic acid and its derivatives, phenoxy ethanol and phenoxy proponol, ethylacetate, clindamycin and meclocycline; sebostats such as flavinoids; hydroxy acids; and bile salts such as scymnol sulfate and its derivatives, deoxycholate, and cholate.

Useful drug actives in the compositions of the present invention include non-steroidal anti-inflammatory drugs (NSAIDS). The NSAIDS can be selected from the following categories: propionic acid derivatives; acetic acid derivatives; fenamic acid derivatives; biphenylcarboxylic acid derivatives; and oxicams. All of these NSAIDS are fully described in the U.S. Pat. No. 4,985,459 to Sunshine et al., issued Jan. 15, 1991, incorporated by reference herein. Most preferred are the propionic NSAIDS including but not limited to aspirin, acetaminophen, ibuprofen, naproxen, benoxaprofen, flurbiprofen, fenoprofen, fenbufen, ketoprofen, indoprofen, pirprofen, carprofen, oxaprozin, pranoprofen, miroprofen, tioxaprofen, suprofen, alminoprofen, tiaprofenic acid, fluprofen and bucloxic acid. Also useful are the steroidal anti-inflammatory drugs including hydrocortisone and the like.

Useful drug actives in the compositions of the present invention include antihistaminic drugs. Antihistaminic drugs preferred for inclusion in compositions of the present invention include pharmaceutically-acceptable salts of chlorpheniramine, triprolidine, diphenhydramine, doxylamine, pyrilamine, phenindamine, promethazine, cyproheptadine, azatadine, clemastine, carbinoxamine, tripelennamine, terfenadine, dexchlorpheniramine, brompheniramine, chlorcyclizine, diphenylpyraline, pheniramine and phenyltoloxamine, and mixtures thereof.

Useful drug actives in the compositions of the present invention include antitussive drugs. Antitussive drugs preferred for inclusion in compositions of the present invention include pharmaceutically-acceptable salts of dextromethorphan, codeine, caramiphen and carbetapentane.

Useful drug actives in the compositions of the present invention include antipruritic drugs. Antipruritic drugs preferred for inclusion in compositions of the present invention include pharmaceutically-acceptable salts of methdilizine and trimeprazine.

Useful drug actives in the compositions of the present invention include anticholinergic drugs. Anticholinergic drugs preferred for inclusion in compositions of the present invention include pharmaceutically-acceptable salts of scopolamine, atropine, homatropine, levodopa, dicyclomine, hyoscyamine, procyclidine, trihexyphenidyl and ethopropazine.

Useful drug actives in the compositions of the present invention include anti-emetic and antinauseant drugs. Anti-emetic and antinauseant drugs preferred for inclusion in compositions of the present invention include pharmaceutically-acceptable salts of cyclizine, meclizine, chlorpromazine, buclizine, metoclopramide, prochlorperazine and trimethobenzamide.

Useful drug actives in the compositions of the present invention include anorexic drugs. Anorexic drugs preferred for inclusion in compositions of the present invention include pharmaceutically-acceptable salts of benzphetamine, phentermine, chlorphentermine, fenfluramine, diethylpropion and phendimetrazine.

Useful drug actives in the compositions of the present invention include central stimulant drugs. Central stimulant drugs preferred for inclusion in compositions of the present invention include pharmaceutically-acceptable salts of amphetamine, methamphetamine, dextroamphetamine and methylphenidate.

Useful drug actives in the compositions of the present invention include antiarrhythmic drugs. Antiarrhythmic drugs preferred for inclusion in compositions of the present invention include pharmaceutically-acceptable salts of propranolol, procainamide, disopyramide, quinidine, encainide, flecanaide, mexiletine and tocainide. Other antiarrhythmic drugs preferred for inclusion in compositions of the present invention include pharmaceutically-acceptable salts of the quinidine derivatives disclosed in U.S. Pat. No. 4,716,171 issued to Jarreau and Koenig on Dec. 29, 1987, which is hereby incorporated herein in its entirety by reference. Highly preferred compounds included in this class include pharmaceutically-acceptable salts of 3S-hydroxy-10,11-dihydroquinidine, 3R-hydroxy-10,11-dihquinidiquinidine, 3R-hydroxy-O-acetyl-10,11-dihydroquinidine, and 3S-hydroxy-O-acetyl-10,11-dihydroquinidine, especially 3S-hydroxy-10,11-dihydroquinidine.

Useful drug actives in the compositions of the present invention include β-adrenergic blocker drugs. β-Adrenergic blocker drugs preferred for inclusion in compositions of the present invention include pharmaceutically-acceptable salts of metoprolol, acebutolol, betaxolol, labetalol and timolol. β-Adrenergic blocker drugs more preferred for inclusion in compositions of the present invention include metoprolol tartrate, acebutolol hydrochloride, betaxolol hydrochloride, labetalol hydrochloride and timolol maleate.

Useful drug actives in the compositions of the present invention include cardiotonic drugs. Cardiotonic drugs preferred for inclusion in compositions of the present invention include pharmaceutically-acceptable salts of milrinone, amrinone and dobutamine. Other cardiotonic drugs preferred for inclusion in compositions of the present invention include pharmaceutically-acceptable salts of 14-amino steroid derivatives, some of which are disclosed in U.S. Pat. Nos. 4,325,879, 4,552,868 and 4,584,289, issued to Jarreau and Koenig on Apr. 20, 1982, Nov. 12, 1985 and Apr. 22, 1986, respectively, each of which are hereby incorporated herein in their entirety by reference.

Useful drug actives in the compositions of the present invention include antihypertensive drugs. Antihypertensive drugs preferred for inclusion in compositions of the present invention include pharmaceutically-acceptable salts of enalapril, clonidine, hydralazine, minoxidil (which is also a hair growth stimulator drug), guanadrel, guanethidine, guanfacine, mecamylamine, methyldopate, pargyline, phenoxybenzamine and prazosin.

Useful drug actives in the compositions of the present invention include diuretic drugs. Diuretic drugs preferred for inclusion in compositions of the present invention include pharmaceutically-acceptable salts of amiloride and hydrochlorothiazide. Diuretic drugs more preferred for inclusion in compositions of the present invention include amiloride hydrochloride.

Useful drug actives in the compositions of the present invention include vasodilator drugs. Vasodilator drugs preferred for inclusion in compositions of the present invention include pharmaceutically-acceptable salts of diltazem, amiodarone, isoxsuprine, nylidrin, tolazoline and verapamil.

Useful drug actives in the compositions of the present invention include vasoconstrictor drugs. Vasoconstrictor drugs preferred for inclusion in compositions of the present invention include pharmaceutically-acceptable salts of dihydroergotamine, ergotamine and methysergide.

Useful drug actives in the compositions of the present invention includes anti-ulcer drugs. Anti-ulcer drugs preferred for inclusion in compositions of the present invention include pharmaceutically-acceptable salts of ranitidine and cimetidine.

Useful drug actives in the compositions of the present invention include anesthetic drugs. Anesthetic drugs preferred for inclusion in compositions of the present invention include pharmaceutically-acceptable salts of lidocaine, bupivacaine, chlorprocaine, dibucaine, etidocaine, mepivacaine, tetracaine, dyclonine, hexylcaine, procaine, cocaine, ketamine, pramoxine and phenol.

Useful drug actives in the compositions of the present invention include antidepressant drugs. Antidepressant drugs preferred for inclusion in compositions of the present invention include pharmaceutically-acceptable salts of imipramine, desipramine, amitriptyline, nortriptyline, protriptyline, doxepin, maprotiline, phenelzine, tranylcypromine, trazodone and trimipramine.

Useful drug actives in the compositions of the present invention include tranquilizer and sedative drugs. Tranquilizer and sedative drugs preferred for inclusion in compositions of the present invention include pharmaceutically-acceptable salts of chlordiazepoxide, benactyzine, benzquinamide, flurazepam, hydroxyzine, loxapine and promazine.

Useful drug actives in the compositions of the present invention include antipsychotic drugs. Antipsychotic drugs preferred for inclusion in compositions of the present invention include pharmaceutically-acceptable salts of chlorprothixene, fluphenazine, haloperidol, molindone, thioridazine and trifluoperazine.

Useful drug actives in the compositions of the present invention include antimicrobial drugs (antibacterial, antifungal, antiprotozoal and antiviral drugs). Antimicrobial drugs preferred for inclusion in compositions of the present invention include pharmaceutically-acceptable salts of β-lactam drugs, quinolone drugs, ciprofloxacin, norfloxacin, tetracycline, erythromycin, amikacin, triclosan, doxycycline, capreomycin, chlorhexidine, chlortetracycline, oxytetracycline, clindamycin, ethambutol, metronidazole, pentamidine, gentamicin, kanamycin, lineomycin, methacycline, methenamine, minocycline, neomycin, netilmicin, paromomycin, streptomycin, tobramycin, miconazole and amanfadine. Antimicrobial drugs preferred for inclusion in compositions of the present invention include tetracycline hydrochloride, erythromycin estolate, erythromycin stearate (salt), amikacin sulfate, doxycycline hydrochloride, capreomycin sulfate, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, amanfadine hydrochloride, amanfadine sulfate, triclosan, octopirox, parachlorometa xylenol, nystatin, tolnaftate and clotrimazole.

Useful drug actives in the compositions of the present invention include antineoplastic drugs. Antineoplastic drugs preferred for inclusion in compositions of the present invention include pharmaceutically-acceptable salts of bleomycin, daunorubicin, doxorubicin, mechlorethamine, procarbazine, quinacrine, tamoxifen, vinblastine and vincristine.

Useful drug actives in the compositions of the present invention include antimalarial drugs. Antimalarial drugs preferred for inclusion in compositions of the present invention include pharmaceutically-acceptable salts of chloroquine, hydroxychloroquine primaquine and quinine.

Useful drug actives in the compositions of the present invention include muscle relaxant drugs. Muscle relaxant drugs preferred for inclusion in compositions of the present invention include pharmaceutically-acceptable salts of cinnamedrine, cyclobenzaprine, flavoxate, orphenadrine, papaverine, mebeverine, idaverine, ritodrine, dephenoxylate, dantrolene and azumolene.

Useful drug actives in the compositions of the present invention include antispasmodic drugs. Antispasmodic drugs preferred for inclusion in compositions of the present invention include pharmaceutically-acceptable salts of the compounds disclosed in U.S. Pat. No. 3,856,825 issued to Wright, Burch and Goldenburg on Dec. 24, 1974, which is hereby incorporated herein in its entirety by reference.

Useful drug actives in the compositions of the present invention include antidiarrheal drugs. Antidiarrheal drugs preferred for inclusion in compositions of the present invention include pharmaceutically-acceptable salts of loperamide.

Useful drug actives in the compositions of the present invention include bone-active drugs. Bone-active drugs preferred for inclusion in compositions of the present invention include pharmaceutically-acceptable salts of diphosphonate drug compounds and phosphonoalkylphosphinate drug compounds, including the prodrug esters thereof. Such compounds are disclosed, for example, in U.S. Pat. Nos. 3,683,080 issued to Francis on Aug. 8, 1972; 4,304,734 issued to Jary, Rihakova & Zobacova on Dec. 8, 1981; 4,687,768 issued to Benedict & Johnson on Aug. 18, 1987; 4,711,880 issued to Stahl & Schmitz on Dec. 8, 1987; and 4,719,203 issued to Bosies & Gall on Jan. 12, 1988; copending U.S. patent application Ser. Nos. 808,584, of Benedict & Perkins filed Dec. 13, 1985; 945,069 of Ebetino, Buckingham & McOsker filed Dec. 19, 1986; 945,068 of Ebetino & Benedict filed Dec. 19, 1986; and 069,666 of Ebetino filed Jul. 6, 1987; and European Patent Application Nos. 0,001,584 of Blum, Hempel & Worms, published May 2, 1979; 0,039,033 published Apr. 11, 1981; 0,186,405 of Benedict & Perkins, published Jul. 2, 1986; and 0,243,173 of Oku, Todo, Kasahara, Nakamura, Kayakiri & Hashimoto, published Oct. 28, 1987; all of which are hereby incorporated herein in their entirety by reference.

Also useful in the present invention are sunless tanning agents including dihydroxyacetone, indole derivatives, and the like. These sunless tanning agents may also be used in combination with conventional sunscreen agents such as those disclosed in Segarin, et al., at Chapter VIII, pages 189 et seq., of Cosmetics Science and Technology, incorporated by reference herein, as well as wound healing agents such as peptide derivatives, yeast, panthenol, Iamin and kinetin.

Other useful skin actives include skin bleaching (or lightening) agents including but not limited to hydroquinone, ascorbic acid, kojic acid and sodium metabisulfite.

Nonionic Polyacrylamide The non-ionic polymers useful in the present invention are polyacrylamides and substituted polyacrylamides, branched or unbranched. These polymers are non-ionic water-dispersable polymers which can be formed from a variety of monomers including acrylamide and methacrylamide which are unsubstituted or substituted with one or two alkyl groups (preferably $C_1$–$C_5$). Preferred acrylate amides and methacrylate amides in which the amide nitrogen is unsubstituted, or substituted with one or two $C_1$–$C_5$ alkyl groups (preferably: methyl, ethyl or propyl), for example, acrylamide, methacrylamide, N-methylacrylamide, N-methylmethacrylamide, N,N-dimethylmethacrylamide, N-isopropylacrylamide, N-isopropylmethacrylamide and N,N-dimethylacrylamide. These monomers are generally disclosed in U.S. Pat. No. 4,963,348 to Bolich, Jr. et al., issued Oct. 16, 1990, incorporated by reference herein in its entirety. These copolymers may optionally be formed using conventional neutral crosslinking agents such as dialkenyl compounds. The use of such crosslinking agents for cationic polymers is disclosed in U.S. Pat. No. 4,628,078 to Glover et al. issued Dec. 9, 1986 and U.S. Pat. No. 4,599,379 to Flesher et al. issued Jul. 8, 1986 both of which are incorporated by reference herein. These non-ionic co-polymers have a molecular weight greater than about 1,000,000 preferably greater than about 1,500,000 and range up to about 30,000,000. Preferably, as a result of being synthesized by reverse phase emulsion polymerization, these non-ionic polyacrylamides are predispersed in a water-immiscible solvent such as mineral oil and the like, containing a high HLB surfactant (HLB from about 7 to about 10) which helps to facilitate water dispersibility of the polyacrylamide. Most preferred for use herein is the non-ionic polymer under the CTFA designation: polyacrylamide and isoparrafin and laureth-7, available as Sepigel from Seppic Corporation.

These non-ionic polyacrylamides are present at a level from about 0.05% to about 20%, preferably from about 0.05% to 5% and most preferably from about 0.1% to about 10%.

Vehicle The compositions of the present invention are used along with pharmaceutically-acceptable carrier (or vehicle) components. The term "pharmaceutically-acceptable carrier components", as used herein, means compatible solid or liquid filler diluents which are suitable for administration to a human or lower animal. The term "compatible", as used herein, means that the components are capable of being commingled with the drug compounds, diols and fatty acids of the compositions of the present invention, and with each other, in a manner such that there is no interaction which would substantially reduce the pharmaceutical efficacy of the compositions of the present invention under ordinary use situations. Pharmaceutically-acceptable carrier components must, of course, be of sufficiently high purity and sufficiently low toxicity to render them suitable for administration to the human or lower animal being treated.

Some examples of substances which can serve as pharmaceutically-acceptable carrier components are polyethylene glycol; glycerol; ethanol; water; antioxidants; surfactants; chelating agents; preservatives; thickeners; as well as other non-toxic compatible substances used in pharmaceutical formulations.

These compositions can also contain one or more humectants/moisturizers many of which may also be useful as pharmaceutical actives. A variety of humectants/moisturizers can be employed and can be present at a level of from about 1% to about 30%, more preferably from about 2% to about 8% and most preferably from about 3% to about 5%. These materials include polyhydroxy alcohols such as sorbitol, glycerin, hexanetriol, propylene glycol, hexylene glycol and the like; polyethylene glycol; sugars and starches; sugar and starch derivatives (e.g. alkoxylated glucose); D-panthenol; hyaluronic acid; lactamide monoethanolamine; acetamide monoethanolamine; and mixtures thereof.

Preferred humectants/moisturizers for use in the compositions of the present invention are the $C_3$–$C_6$ diols and triols. Especially preferred is the triol, glycerin. The compositions of this invention may also contain pharmaceutically acceptable optional components that modify the physical and/or therapeutic effects of the compositions. Such optional components may include, for example, additional solvents, emulsifiers, gelling agents, fragrances, preservatives, and stabilizers. However, such optional materials must not unduly interfere with the transdermal delivery of the drug active. Optional components useful in the compositions of this invention are described in the following patent documents, incorporated by reference herein: European Patent Publication 43,738, Wickett et al., published Jan. 13, 1982; and U.S. Pat. No. 4,552,872, Cooper et al., issued Nov. 12, 1985.

Most preferred compositions herein are gel-type compositions.

Another optional material is a solvent or co-solvent material. Such solvent materials include, for example, short chain alcohols and ethers. Preferred optional solvent materials include polyethylene glycols, dipropylene glycol, ethylene glycol monoethyl ether, ethanol, isopropanol, and dimethyl isosorbide. Water may also be used as a solvent or co-solvent in the compositions of this invention. If water is used in a saturated system, a gel or emulsion is preferably formed.

Most preferred compositions have a pH of below about 5, preferably below about 4, and most preferably below about 3.

While particular embodiments of the present invention have been described, it will be obvious to those skilled in the art that various changes and modifications to the compositions disclosed herein can be made without departing from the spirit and the scope of the invention. It is intended to cover, in the appended claims, all such modifications that are within the scope of this invention.

Test Method

Transdermal penetration of drugs is conveniently determined and compared from various vehicles using the apparatus and procedure described below.

Full thickness excised human thigh skin is obtained from cadavers after all hair had been clipped and the skin washed. The skin samples are then bathed in 10% glycerin and stored frozen. The glycerin prevents the formation of ice crystals which could possibly damage the keratinized cells and/or the intercellular lipid matrix. After a rapid thawing, the skin is conditioned for 24 hours in Hank's Balanced Salt Solution with 1% antibacterial-antimycotic solution. Then the skin is washed with distilled water. A single skin donor is used for each experiment, and individual sections for use are selected based on integrity of the stratum corneum (visual determination). Selected areas are cut to 1cm$^2$ using a scalpel.

Tests are conducted using glass diffusion cells placed in temperature-regulated stirring modules. Skin sections are mounted in the cells, and the receptor phase is added. The receptor phase is 50% Hank's Balance Salt Solution with 1% antibiotic-antimycotic solution. Each diffusion cell has an exposed area of 0.79cm$^2$ and a receptor capacity of 5ml.

Sufficient formulation is applied (750 ul) to the surface of the skin to ensure infinite dose conditions, and the diffusion cell is covered with plastic wrap or parafilm to prevent product evaporation. At each sampling time the receptor phase is removed for analysis of drug content. The receptor phase is removed for analysis of drug content. The receptor phase is replenished at each sampling time in order to maintain sink conditions. Preferably 3 to 6 replicates are run with sampling intervals occurring at 1, 2, 4 & 6 hours.

Penetration rate (Flux) is determined as the quantity of drug penetrating a measured area of skin per hour during the 5 hour interval between 1 hour and 6 hours. Generally steady state is reached before 1 hour. Penetration rate is usually expressed as ug drug per cm$^2$ skin per hour.

The following examples further describe and demonstrate embodiments within the scope of the present invention. The examples are given solely for the purpose of illustration and are not to be construed as limitations of the present invention, as many variations thereof are possible without departing from the spirit and scope of the invention.

Ingredients are identified by chemical or CTFA name.

EXAMPLES

Example I

An anti-acne composition is made by combining the following ingredients.

| Ingredient | (% W/W) |
| --- | --- |
| Water, Purified | 52.395 |
| Alcohol SDA 40 | 40.000 |
| Polyacrylamide and $C_{13-14}$ Isoparaffin and Laureth-7 | 4.000 |
| Salicylic Acid | 2.000 |
| Glycerin | 1.000 |
| Aloe Vera Gel | 0.500 |
| Menthol | 0.100 |
| Disodium EDTA | 0.005 |

The alcohol is added to a suitable size container. Using a Lightnin' mixer with a 3 blade paddle prop, the salicylic acid is added to the alcohol and mixed at low speed (100 rpm) until the salicylic acid is dissolved. Menthol is added to the alcohol and mixed until dissolved. Separately, water is added to a suitable size container. Aloe vera gel and disodium EDTA are added to the water and mixed at low speed (100 rpm) until completely dissolved. The water phase is then added to the alcohol phase and mixed until clear. Gylcerin is added and mixed until clear. While mixing at moderate speed (300 rpm), the polyacrylamide and $C_{13-14}$ isoparaffin and laureth-7 is added to form a gel. The resulting gel is mixed at moderate speed until uniform.

Example II

An anti-acne and/or analgesic composition is made by combining the following ingredients utilizing conventional mixing techniques as described above in Example I.

| Ingredient | (% W/W) |
| --- | --- |
| Water, Purified | 55.0 |
| Ibuprofen | 2.0 |
| Alcohol SDA 40 | 40.0 |

-continued

| Ingredient | (% W/W) |
| --- | --- |
| Polyacrylamide and C$_{13-14}$ Isoparaffin and Laureth-7 | 3.0 |

The compositions display skin penetration of the Ibuprofen active as well as improved skin feel and residue characteristics together with excellent moisturizing, emolliency, rub-in and absorption characteristics.

Example III

A keratolytic composition for dermatological disorders is made by combining the following ingredients utilizing conventional mixing techniques as described above in Example I.

| Ingredient | (% W/W) |
| --- | --- |
| Water | 86.5 |
| Urea | 10.0 |
| Benzyl Alcohol | 0.5 |
| Polyacrylamide and C$_{13-14}$ Isoparaffin and Laureth-7 | 3.0 |

The compositions display skin penetration of the Urea active as well as improved skin feel and residue characteristics together with excellent moisturizing, emolliency, rub-in and absorption characteristics.

Example IV

A composition for sunless tanning is made by combining the following ingredients utilizing conventional mixing techniques as described above in Example I.

| Ingredient | (% W/W) |
| --- | --- |
| Water | 91.5 |
| Benzyl Alcohol | 0.5 |
| Polyacrylamide and C$_{13-14}$ Isoparaffin and Laureth-7 | 3.0 |
| Dihydroxyacetyone | 3.0 |
| Glycerin | 2.0 |

The compositions display improved skin penetration of the dihydroxyacetone as well as improved skin feel and residue characteristics together with excellent moisturizing, emolliency, rub-in and absorption characteristics.

What is claimed is:

1. A topical pharmaceutical composition having enhanced penetration through the skin, comprising:

(a) an aqueous carrier comprising from about 53% to about 91.5% water;

(b) a safe and effective amount of a sunless tanning agent; and (c) from about 0.05% to about 5% of a non-ionic polyacrylamide having a molecular weight of from about 1,000,000 to about 30,000,000, the polyacrylamide being predispersed in a water-immiscible oil containing a surfactant having an HLB of from about 7 to about 10, wherein the composition is in gel emulsion form and has a pH below about 5.

2. The composition of claim 1 wherein the polyacrylamide comprises monomers selected from acrylamide and methacrylamide which are unsubstituted or substituted with at least one alkyl group having from about 1 to about 5 carbon atoms.

3. The composition of claim 2 wherein the polyacrylamide comprises monomers selected from the group consisting of acrylamide, methacrylamide, N-methylacrylamide, N-methylmethacrylamide, N,N-dimethylmethacrylamide, N-isopropylacrylamide, N-isopropylmethacrylamide and N,N-dimethylacrylamide.

4. The composition of claim 3 wherein the polyacrylamide has a molecular weight greater than about 1,500,000.

5. A composition according to claim 1 which further comprises from about 1% to about 30% propylene glycol.

6. A composition according to claim 1 wherein said sunless tanning agent is selected from the group consisting of dihydroxyacetone and indole derivatives.

7. A composition according to claim 5 wherein said sunless tanning agent is selected from the group consisting of dihydroxyacetone and indole derivatives.

8. A composition according to claim 1 wherein said sunless tanning agent is dihydroxyacetone.

9. A composition according to claim 5 wherein said sunless tanning agent is dihydroxyacetone.

10. A composition according to claim 1, wherein the aqueous carrier further comprises polyethylene glycol, glycerol or ethanol.

11. A composition according to claim 1, wherein the nonionic polyacrylamide is dispersed in isoparaffin and laureth-7.

12. A composition according to claim 1, comprising from about 0.1% to 5% of the non-ionic polyacrylamide.

13. A composition according to claim 1, comprising from about 0.1% to about 10% of the sunless tanning agent.

14. A composition according to claim 1, comprising from about 0.1% to about 5% of the sunless tanning agent.

15. The composition of claim 1 which further comprises a sunscreen active.

* * * * *

UNITED STATES PATENT AND TRADEMARK OFFICE
CERTIFICATE OF CORRECTION

PATENT NO. : 5,776,485
DATED : July 7, 1998
INVENTOR(S) : George E. Deckner et al.

It is certified that error appears in the above-identified patent and that said Letters Patent is hereby corrected as shown below:

At column 3, line 31 "250C" should read --25°C--.

At column 5, line 20 "dihquinidiquinidine" should read --dihydroquinidine--.

Signed and Sealed this

Twenty-seventh Day of October, 1998

Attest:

BRUCE LEHMAN

*Attesting Officer*          *Commissioner of Patents and Trademarks*